United States Patent [19]
Cleary

[11] Patent Number: 5,964,588
[45] Date of Patent: *Oct. 12, 1999

[54] TELESCOPING, INTRA-ORAL FORCE MODULE

[75] Inventor: James D. Cleary, Glendora, Calif.

[73] Assignee: 3M Innovative Properties Company, St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 09/063,947

[22] Filed: Apr. 21, 1998

[51] Int. Cl.⁶ .................................................... A61C 3/00
[52] U.S. Cl. ............................................. 433/19; 433/18
[58] Field of Search .................................. 433/18, 19, 21, 433/24

[56] References Cited

U.S. PATENT DOCUMENTS

| | | | |
|---|---|---|---|
| 934,958 | 9/1909 | Case | 433/7 |
| 3,618,214 | 11/1971 | Armstrong | 433/19 |
| 3,798,773 | 3/1974 | Northcutt | 433/19 |
| 4,462,800 | 7/1984 | Jones | 433/19 |
| 4,551,095 | 11/1985 | Mason | 433/19 |
| 4,708,646 | 11/1987 | Jasper | 433/19 |
| 4,795,342 | 1/1989 | Jones | 433/19 |
| 4,815,972 | 3/1989 | Howe | 433/5 |
| 5,183,388 | 2/1993 | Kumar | 433/19 |
| 5,352,116 | 10/1994 | West | 433/19 |
| 5,435,721 | 7/1995 | Vogt | 433/19 |
| 5,562,445 | 10/1996 | DeVincenzo et al. | 433/19 |
| 5,645,423 | 7/1997 | Collins, Jr. | 433/21 |
| 5,645,424 | 7/1997 | Collins, Jr. | 433/21 |
| 5,651,672 | 7/1997 | Cleary et al. | 433/19 |
| 5,678,990 | 10/1997 | Rosenberg | 433/19 |
| 5,711,667 | 1/1998 | Vogt | 433/19 |
| 5,718,576 | 2/1998 | Schnaitter et al. | 433/22 |
| 5,738,514 | 4/1998 | DeVincenzo et al. | 433/19 |

FOREIGN PATENT DOCUMENTS 2702141A  9/1994  France .

OTHER PUBLICATIONS

Eureka Spring! Clinical Information, May 1996.

*Primary Examiner*—Nicholas D. Lucchesi
*Attorney, Agent, or Firm*—James D. Christoff

[57] ABSTRACT

An intra-oral device for applying a force to the mandibular and maxillary dental arches includes a first member and a second member slidably received in the first member. A spring extends around the second member for urging the second member and the first member in directions away from each other. A third member is slidably received in the second member and preferably is detachable from the second member before installation of the device in the oral cavity in order to cut, bend or make other alterations of its shape.

28 Claims, 6 Drawing Sheets

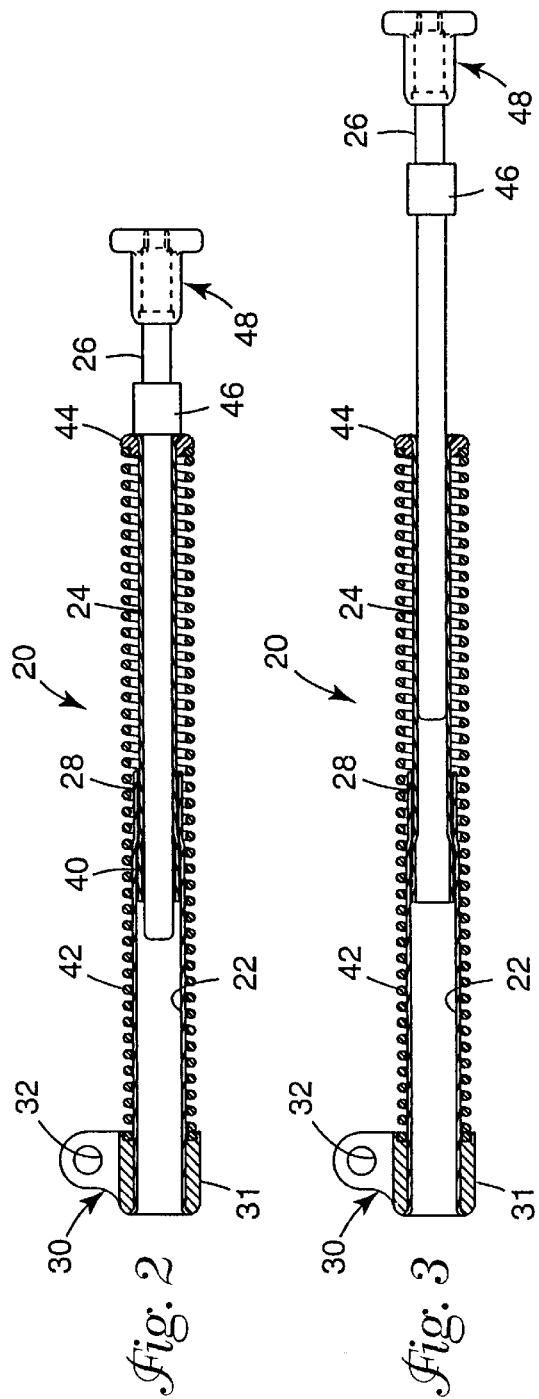

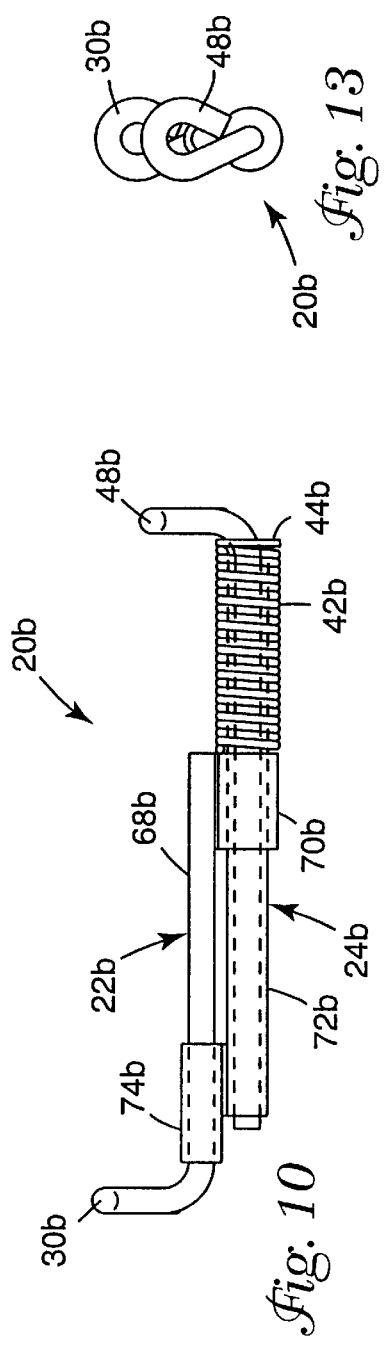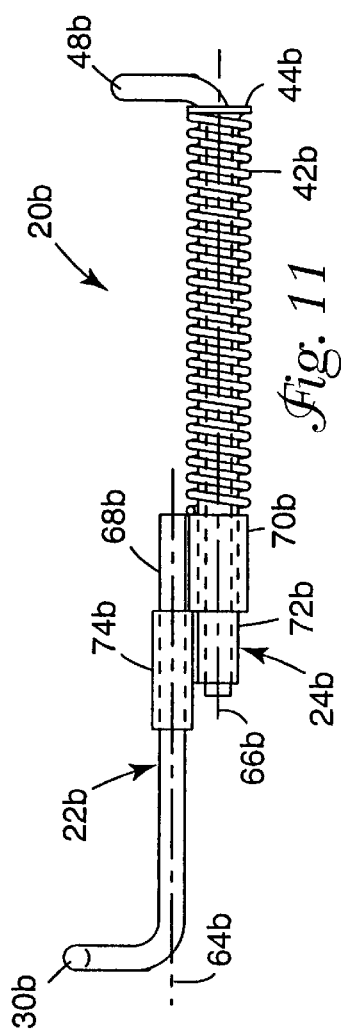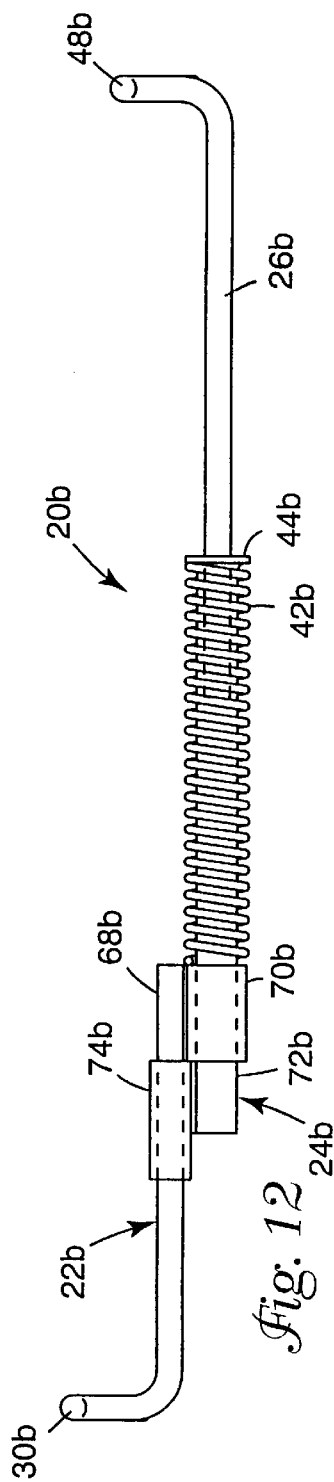

TELESCOPING, INTRA-ORAL FORCE MODULE

BACKGROUND OF THE INVENTION

1. Field of the Invention

This invention relates to a device useful during orthodontic treatment for correcting the position of one dental arch relative to the other. More specifically, this invention relates to a force module device for urging the lower dental arch either in a forwardly or a rearwardly direction relative to the upper dental arch in order to improve occlusion.

2. Description of the Related Art

Orthodontic treatment involves movement of malpositioned teeth to orthodontically correct positions. During treatment, tiny orthodontic appliances known as brackets are often connected to anterior, cuspid and bicuspid teeth, and an archwire is placed in a slot of each bracket. The archwire forms a track to guide movement of the brackets and the associated teeth to desired positions for correct occlusion. Typically, the ends of the archwire are held by appliances known as buccal tubes that are secured to the patient's molar teeth. The brackets, archwires and buccal tubes are commonly referred to as "braces".

The orthodontic treatment of some patients include correction of the alignment of the upper dental arch with the lower dental arch. For example, certain patients have a condition referred to as a Class II malocclusion where the lower dental arch is located an excessive distance in a rearwardly direction relative to the location of the upper dental arch when the jaws are closed. Other patients may have an opposite condition referred to as a Class III malocclusion wherein the lower dental arch is located in a forwardly direction of its desired location relative to the position of the upper dental arch when the jaws are closed.

Orthodontic treatment of Class II and Class III malocclusions are commonly corrected by movement of the upper dental arch as a single unit relative to movement of the lower dental arch as a single unit. To this end, forces are often applied to each dental arch as a unit by applying force to the brackets or buccal tubes, the archwires, or attachments connected to the brackets, buccal tubes, or archwires. In this manner, a Class II or Class III malocclusion can be corrected at the same time that the archwires and the brackets are used to move individual teeth to desired positions relative to each other.

Correction of Class II and Class III malocclusions is sometimes carried out by use of a force-applying system known as headgear that includes strapping which extends around the rear of the patient's head. The strapping is often connected by tension springs that, in turn, are connected to the buccal tubes, the brackets or one of the archwires. Additionally, as an alternative for correction of Class III malocclusions, the strapping may be connected by tension springs to a chin cup that externally engages the patient's chin. In either instance, the strapping and springs serve to apply a rearwardly-directed force to the associated jaw.

However, headgear is often considered unsatisfactory because it is visibly apparent. Headgear may serve as a source of embarrassment, particularly among child and teenage patients who may experience teasing from classmates. The embarrassment can be somewhat reduced if the orthodontist instructs the patient to wear the headgear only at night, but unfortunately such practice may lengthen treatment time since the desired corrective forces are applied during only a portion of each calendar day.

Consequently, many practitioners and patients favor the use of intra-oral devices for correcting Class II and Class III malocclusions. Such devices are often located near the cuspid, bicuspid and molar teeth and away from the patient's anterior teeth. As a result, intra-oral devices for correcting Class II and Class III malocclusions are hidden in substantial part once installed and eliminate much of the patient embarrassment that is often associated with headgear.

Orthodontic force modules made of an elastomeric material have been used in the past to treat Class II and Class III malocclusions by connecting a pair of such force modules between the dental arches on opposite sides of the oral cavity. Elastomeric force modules are often used in tension to pull the jaws together in a direction along references lines that extend between the points of attachment of each force module. Such force modules may be an O-ring or a chain-type module made of a number of integrally connected O-rings. However, these modules are typically removable by the patient for replacement when necessary, since the module may break or the elastomeric material may degrade during use to such an extent that the amount of tension exerted is not sufficient.

Unfortunately, orthodontic devices such as headgear and removable force modules are not entirely satisfactory for use with some patients, because the effectiveness of the devices is dependent upon the patient's cooperation. Neglect of the patient to faithfully wear the headgear each day or install new elastomeric force modules as appropriate can seriously retard the progress of treatment and defeat timely achievement of the goals of an otherwise well-planned treatment program, resulting in an additional expenditure of time for both the patient and the orthodontist.

As a result, a number of intra-oral devices that are non-removable by the patient have been proposed in the past to overcome the problems of patient cooperation associated with headgear and with removable intra-oral force modules. For example, U.S. Pat. Nos. 4,708,646, 5,352,116, 5,435, 721 and 5,651,672 describe intra-oral devices with flexible members that are connected to upper and lower dental arches of a patient. The length of the members is selected such that the member is curved in an arc when the patient's jaws are closed. The members have an inherent bias that tends to urge the members toward a normally straight orientation to provide a force that pushes one dental arch forwardly or rearwardly relative to the other dental arch when the jaws are closed.

U.S. Pat. Nos. 5,645,424 and 5,678,990 describe intra-oral devices for correcting Class II and Class III malocclusions having linkage that includes pivotal connections. The devices in both of these references have a somewhat overall "Z" shaped configuration. A device having a somewhat similar overall configuration is shown in U.S. Pat. No. 5,645,423 and includes double helical loops located on each side of a central segment. In U.S. Pat. No. 5,678,990, one of the linkages comprises a spring-loaded telescoping assembly.

Other orthodontic devices for correcting Class II and Class III malocclusions are described in U.S. Pat. Nos. 3,798,773, 4,462,800 and 4,551,095. The devices described in these references include telescoping tube assemblies that urge the dental arches toward positions of improved alignment. The assemblies are securely coupled to other orthodontic appliances such as brackets or buccal tubes by the practitioner, and the problems of patient non-compliance are avoided.

Another type of telescoping tube assembly for repositioning the dental arches is described in U.S. Pat. No. 5,711,667.

In this patent, a spring is provided to urge a plunger in a direction away from a cylinder to achieve desired movements of the patient's teeth. The spring is described in this reference as being located within the cylinder or external of the cylinder in either coaxial relation or offset, parallel relation to the central axis of the plunger.

U.S. Pat. No. 5,562,445 describes another intra-oral device for moving the position of one dental arch relative to the other. The device disclosed in U.S. Pat. No. 5,562,445 includes first and second telescoping cylinders and a plunger received in the first cylinder. A spring in the first cylinder urges the plunger and the first cylinder in directions away from each other, while the first cylinder and the second cylinder are freely slidable relative to each other.

Although a variety of devices including intra-oral telescoping assemblies for correcting Class II and Class III malocclusions have been suggested in the past as noted above, there is a continued need in the art to improve existing options and to provide new devices that represent alternatives for treatment Preferably, such new alternatives would function reliably and efficiently so treatment time is not lengthened, yet also be of simplified construction that would not be prone to breakage or cause difficulties during its manufacture.

SUMMARY OF THE INVENTION

The present invention is related in one aspect to an intra-oral force module for moving the relative positions of the madibular and maxillary dental arches. The force module includes a first tubular member and a second tubular member having a portion slidably received in the first member. A third member has a portion slidably received in the second member. The force module also includes a helical spring extending around the second member for urging the second member and the first member in directions away from each other.

Another aspect of the present invention is directed toward an intra-oral force module for moving the relative positions of the mandibular and maxillary dental arches that includes a first elongated member having a tubular section and an outer end portion for connection to one of the patient's dental arches. The force module also includes a second elongated member having a tubular section and received at least partially in the tubular section of the first member. The second member is longitudinally slidable in the tubular section of the first member. A third elongated member is received at least partially in the tubular section of the second member and is longitudinally slidable in the tubular section of the second member. The third member has an outer end portion for connection to the remaining dental arch of the patient. The force module also includes a spring extending externally around the second member. The spring has a first end portion connected to the first member and a second end portion connected to the second member for urging the first member and the second member in directions away from each other.

The present invention is an advantage, in that the third member is free to move and is not, by itself, necessarily subject to the influence of the spring. Moreover, the three members allow the jaws to be opened widely without separation of one member relative to the other two members. Preferably, however, the third member is separable from the other two members before the force module is installed in the oral cavity. For example, it may be desired to remove the third member in order to trim the length of the third member or to bend the third member to an appropriate curvature as may be needed in some instances.

These and other aspects of the invention are described in more detail below and are shown in the accompanying drawings.

BRIEF DESCRIPTION OF THE DRAWINGS

FIG. 1 is a side elevational view of a telescoping intra-oral force module device constructed in accordance with the present invention, wherein first, second and third elongated members of the device are shown as fully compressed for purposes of illustration;

FIG. 1a is a view somewhat similar to FIG. 1 showing an alternative embodiment of the invention.

FIG. 2 is a side cross sectional view of the intra-oral force module illustrated in FIG. 1 except that the first and second member have moved apart from each other to their fully extended positions;

FIG. 3 is a view somewhat similar to FIG. 2 except that the third member has also been extended;

FIG. 10 is a side elevational view of a telescoping intra-oral force module device according to yet another embodiment of the invention;

FIG. 11 is a view somewhat similar to FIG. 10 except that first and second members of the force module have moved away from each other to fully extended positions;

FIG. 12 is a view somewhat similar to FIG. 11 except that a third member of the force module has been moved outwardly to an extended position; and FIG. 13 is an end elevational view of the force module illustrated in FIGS. 10–12.

DETAILED DESCRIPTION OF THE PREFERRED EMBODIMENTS

Figure 4:
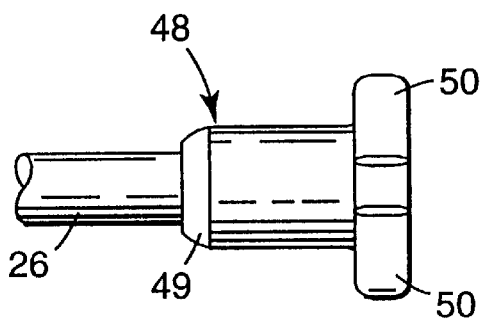
FIG. 4 is an enlarged side elevational view of a connector for use with the force module shown in FIGS. 1–3 for coupling an outer end of the third member to an orthodontic archwire, auxiliary wire or other orthodontic structure in the oral cavity.

An intra-oral device for applying force to the mandibular and maxillary jaws is shown in FIGS. 1–3 and 7–8 and is broadly designated by the numeral 20. The force module device 20 (also called "force module") includes a first elongated member 22, a second elongated member 24 and a third elongated member 26 as can be observed by referring to FIGS. 1–3.

The first elongated member 22 is made of a section of tubular material having a cylindrical configuration. The first member 22 has an inner, narrowed end portion 28 with an inner diameter that is slightly smaller than inner diameter of the remaining extent of the first member 22 as shown in FIGS. 2 and 3. The first member 22 also has an outer end portion that is secured to a first connector 30 for coupling the first member 22 to an orthodontic appliance that is connected to the patient's upper or lower dental arch.

The connector 30 includes a tubular segment 31 that is secured to the outer end portion of the first member 22 in surrounding relation. The connector 30 also has a outwardly extending tab with a hole 32 for receiving a ball pin, a section of wire or other structure for securing the member 22 to the chosen dental arch. In the embodiment shown in FIGS. 1–3 and 6–8, the tab extends outwardly in a lateral direction relative to the central, longitudinal axis of the first member 22, although it should be understood in this regard that as an alternative the tab may extend outwardly from the first member 22 in a direction along its longitudinal axis.

Figure 6:
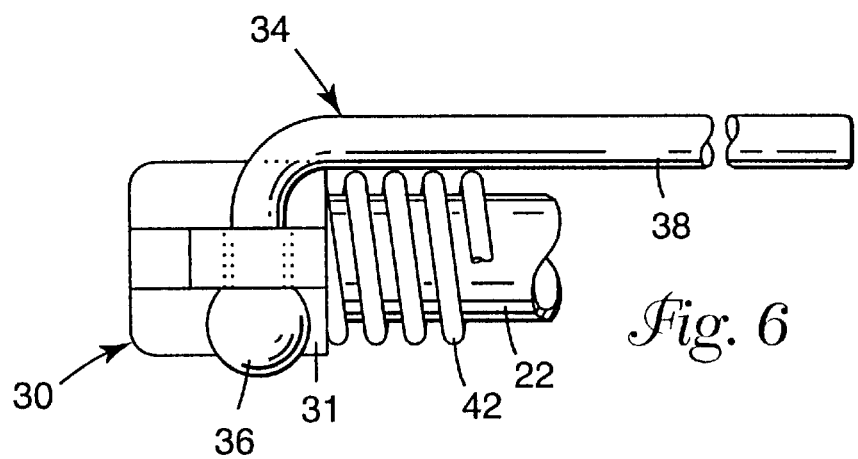
FIG. 6 is an enlarged plan view of another connector of the force module shown in FIGS. 1–3 along with a ball pin for coupling the connector to an orthodontic appliance.

FIG. 6 is an enlarged top view illustrating the connector 30 along with a pin 34 for coupling the connector 30 to an orthodontic appliance such as a buccal tube. The pin 34 includes a shank that extends through the hole 32 of the connector 30. An enlarged head 36 of the pin 34 retains the connector 30 on the pin shank. The shank is also bent to a generally "L"-shaped configuration and has an outer end section 38 remote from the head 36 of a size that is adapted to fit in a passage of a buccal tube, headgear tube or other orthodontic appliance that is fixed to the selected dental arch.

A number of variations of the connector 30 are also possible. As one example, the outwardly extending tab of the connector 30 could be oriented such that the central axis of the hole 32 is parallel to the central axis of the first member 22. As other alternatives, the connector 30 may have a pair of jaw-like arms that are initially open but are adapted to be crimped to a closed orientation for coupling to an orthodontic appliance such as an archwire, an auxiliary wire or other structure. Moreover, the pin 34 can be replaced with other coupling devices such as removable fasteners, a section of ligature wire, or a yieldable, or resilient coupling.

Referring again to FIGS. 1–3, the second elongated member 24 also is preferably made of a cylindrical section of tubular material. The second member 24 is partially received in the first member 22 in sliding, telescoping relation. The second member 24 is movable relative to the first member 22 from the fully compressed position as depicted in FIG. 1 to the fully extended position as shown in FIG. 2.

The second member 24 has an inner, enlarged end portion 40 with an outer diameter that is larger than the outer diameter of the remaining extent of the second member 24. In addition, the outer diameter of the end portion 40 is larger than the inner diameter of the end portion 28 of the first member 22. As such, the inner end portion 40 functions as a stop to limit outwardly movement of the second member 24 relative to the first member 22 and to also prevent separation of the members 22, 24.

The force module 20 also includes a helical compression spring 42 that extends externally around the members 22, 24. An outer end of the spring 42 bears against the connector 30 and is received in a circular recess of the connector 30 adjacent the first member 22. The opposite end of the spring 42 bears against an annular fitting 44 that is secured to an outer end section of the second member 24. Preferably, an outer end of the second member 24 and an outer end of the first member 22 are slightly flared to ensure that the fitting 44 and the connector 30 remain securely coupled to the members 24, 22 respectively.

The third member 26 is partially received in the second member 24 and is movable in a longitudinal direction along the central, longitudinal axis of the second member 24. The third member 26 as shown in the illustrated embodiment is solid, but alternatively could be made using a section of tubular material. Preferably, the third member 26 has an outer diameter that is slightly smaller than the inner diameter of the second member 24 in order to allow the third member 26 to slide freely in the second member 24. Preferably, the adjacent end of the third member 26 is flush with the outer end of the tubular segment 31 when the force module 20 is fully compressed as depicted in FIG. 1 so that the third member 26 functions to push food debris or the like out of the connector 30.

The third member 26 includes a collar 46 that functions; as a stop to limit movement of the third member 26 relative to the second member 24 in directions toward the connector 30. In FIG. 2, the third member 26 is illustrated as having reached a fully retracted position (i.e., has reached its inwardly limit of travel in a direction toward the connector 30). FIG. 3 is an example of an extended position of the third member 26 relative to the second member 24, although other extended positions are also possible.

Figure 5:
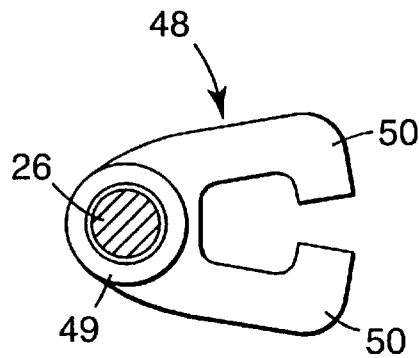
FIG. 5 is an end elevational view of the connector depicted in FIG. 4.

A second connector 48 is secured to an outer end section of the third member 26 and is shown in detail in FIGS. 4 and 5 as it initially appears before installation in the oral cavity. The connector 48 includes a tubular section 49 that surrounds an outer end section of the third member 26. The tubular section is fixed to the outer end section of the third member 26 by a brazing, welding or crimping operation.

As depicted in FIGS. 4 and 5, the second connector 48 includes a pair of opposed arms 50 having a somewhat "L"-shaped configuration. The arms 50 are shown in FIGS. 4 and 5 in their initial orientation wherein the outer ends of the arms 50 are spaced sufficiently apart to receive an orthodontic appliance such as archwire, an auxiliary wire or other device. The arms 50 are bendable toward each other using a hand instrument such as a pair of pliers or the like.

Figure 5A:
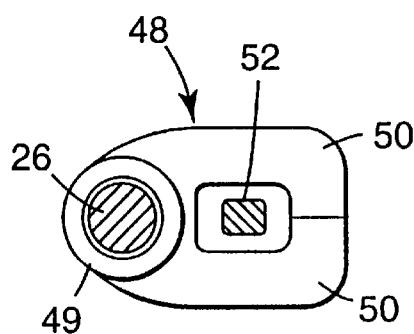
FIG. 5a is a view somewhat similar to FIG. 5 except that a pair of arms of the connector have been closed to surround an archwire.

In FIG. 5a, the arms 50 have been moved to a closed position in order to completely surround an archwire 52. In the closed position of the arms 50 as shown in the drawings, the arms 50 do not tightly engage the archwire 52 but instead leave a clearance space to preclude secure engagement with the wire 52. As such, the connector 48 is freely slidable along the wire 52 as may be desired during opening or closing movement of the patient's jaws.

The connector 48 may be secured to the outer end of the third member 26 by the manufacturer or optionally by the practitioner. For example, it may be preferable for the manufacturer to supply the third member 26 in two or more different overall lengths in order to allow the practitioner to choose a size that would best fit the oral cavity of a particular patient. In that case, the manufacturer may elect to permanently secure the second connector 48 to the outer end section of the third member 26.

Alternatively, it may be preferable for the manufacturer to supply the force module 20 with the third member 26 available in only a single length. The practitioner may then trim the outer end of the third member 26 as needed to enable the device 20 to best fit the oral cavity of a particular patient. In that instance, the connector 48 is supplied as separable or as initially detached from the third member 26, and once the third member 26 is trimmed as appropriate the practitioner can fix the second connector 48 to the third member 26 by crimping, soldering, welding or other means. As another alternative, the manufacturer could permanently secure the second connector 48 to the outer end section of the third member 26, and the practitioner could trim the inner end of the third member 26 as needed and then fix the collar 46 at the desired location to best fit the patient's oral cavity.

Figure 7:
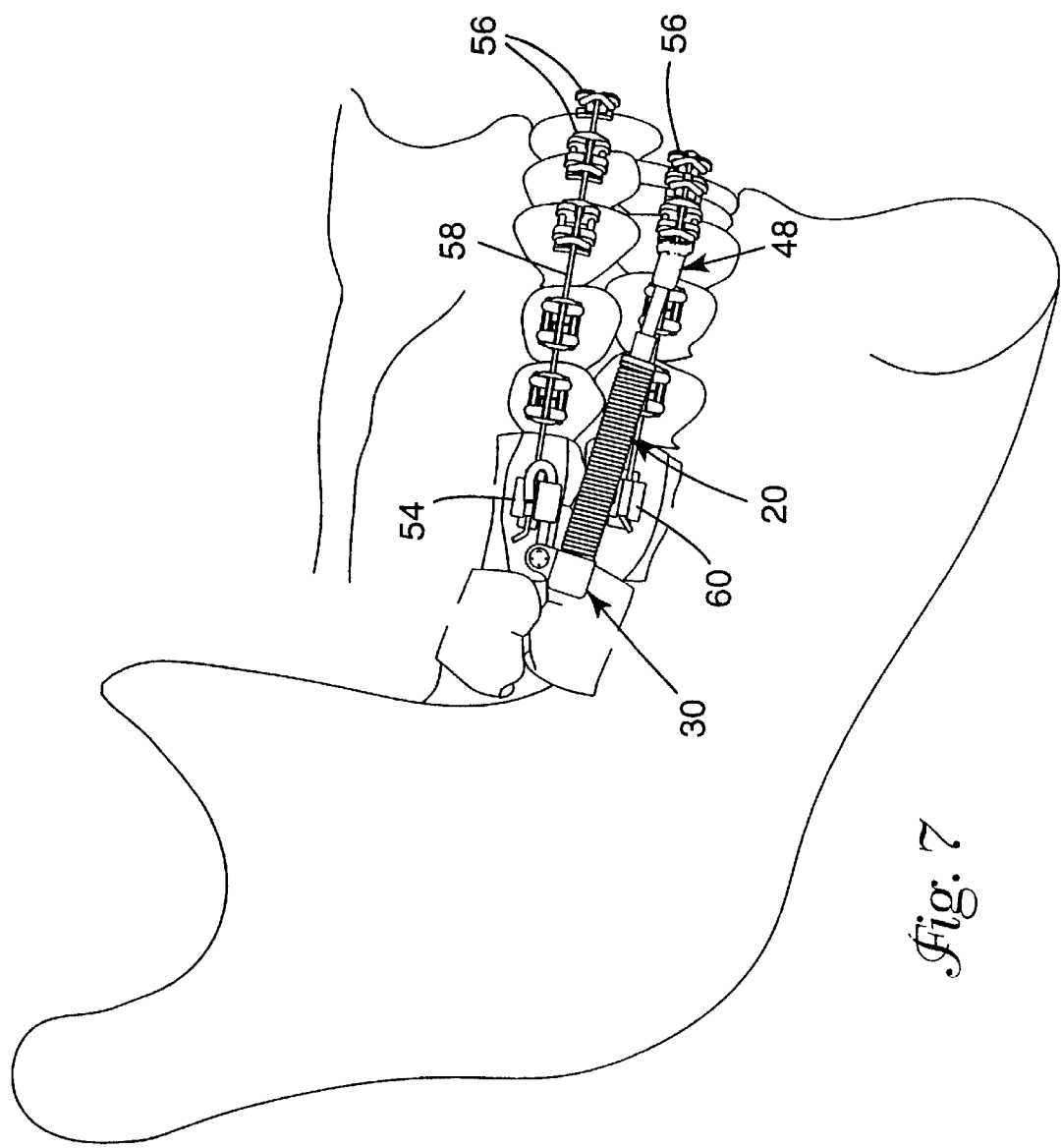
FIG. 7 is a reduced side view in partially schematic form of the force module shown in FIGS. 1–3 when installed in the oral cavity of a patient for applying a force to the mandibular jaw in a forwardly direction relative to the maxillary jaw.
Figure 8:
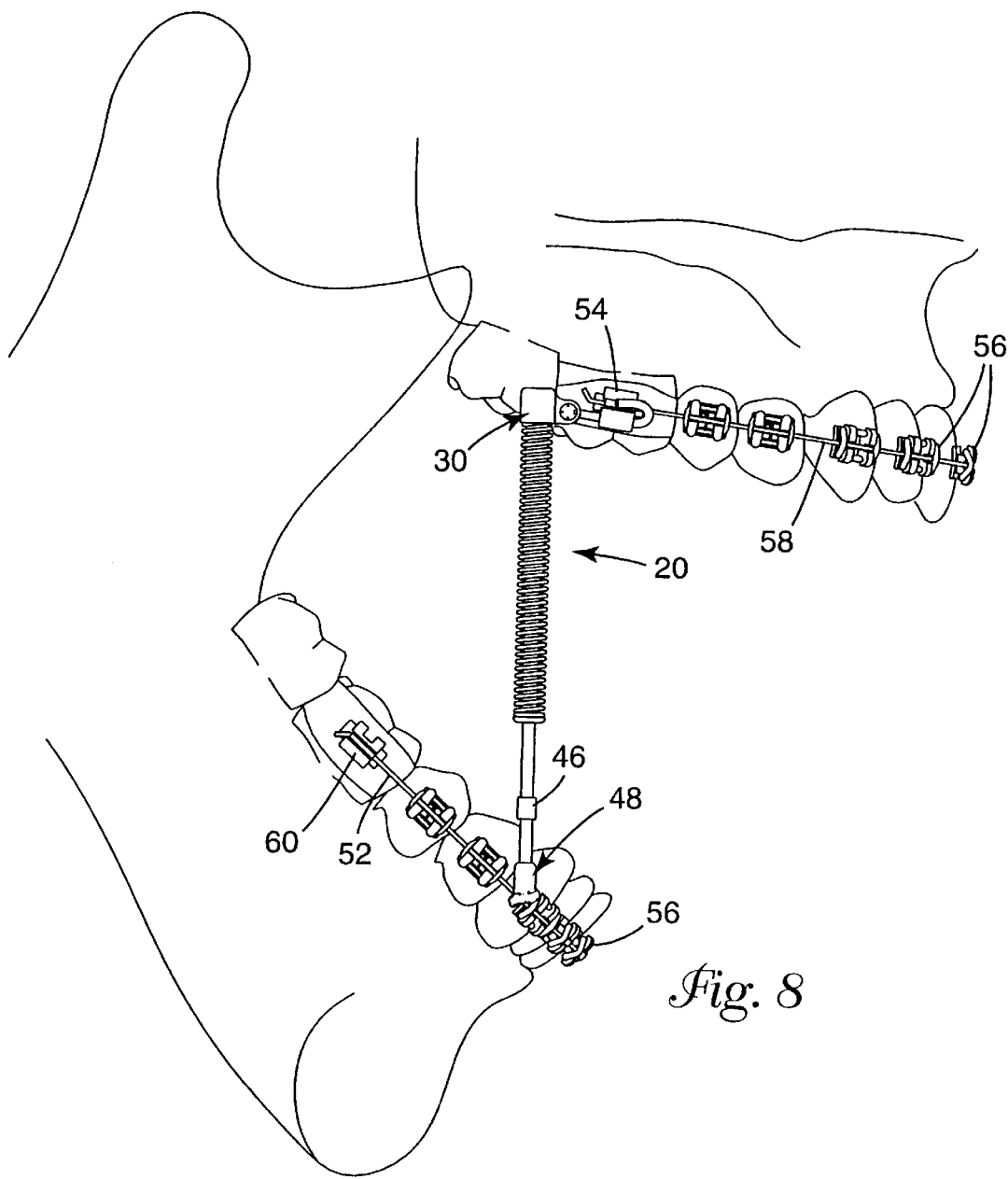
FIG. 8 is a view somewhat similar to FIG. 7 except that the patient's jaws have been opened.

FIGS. 7 and 8 schematically illustrate the force module 20 as installed in the oral cavity between the patient's dental arches. As shown for exemplary purposes, the connector 30 of the force module 20 is coupled to a buccal tube 54 that, in turn, is secured to an orthodontic band that encircles the patient's upper right first molar tooth. In particular, the pin 34 (FIG. 6) has been inserted in a mesial direction (i.e., in a direction toward the center of the patient's dental arch) through a headgear passage or other passage of the buccal tube 54. Once the pin 34 is inserted into the passage of the buccal tube 54, an outer tip of the pin 34 is bent with a hand instrument into an arc in order to prevent the pin 34 from inadvertently detaching from the buccal tube 54.

FIGS. 7 and 8 also show a series of brackets 56 that have been mounted on the patient's upper teeth and the patient's lower teeth. An upper orthodontic archwire 58 is inserted into the slots of the brackets 56 affixed to the patient's upper teeth and also into a passage of the upper buccal tube 54. Similarly, the lower archwire 52 has been inserted into the slots of the brackets 56 that have been mounted on the patient's lower teeth as well as into a passage of a buccal tube 60 that is secured by a band to the patient's lower right first molar tooth.

The second connector 48 of the force module 20 is secured to the lower archwire 52 between an adjacent pair of brackets 56. In particular, the arms 50 of the connector 48 have been crimped as shown in FIG. 5*a* to a closed position in order to surround the lower archwire 52 and yet also provide free sliding movement of the connector 48 along the archwire 52 in the space between the adjacent brackets 56. Optionally, the arms 50 are slightly bent with a hand instrument relative to the longitudinal axis of the force module 20 as shown in FIGS. 7–8 in order to provide greater clearance around the archwire 52 once the arms 50 are moved to a closed position.

As another option, the third member 26 may be bent in an arc (for example, in an arc of approximately 20° about its longitudinal axis) at a location outwardly of the collar 46. Bending of the third member 26 in this manner may, in some instances, provide a better fit in accordance with the size and orientation of the patient's dental arches as well as in accordance with the particular orientation of adjacent teeth. The third member 26 can be bent by the practitioner or supplied in bent shape by the manufacturer, or alternatively may be used in its straight orientation as illustrated in FIGS. 1–3.

Before installation of the force module 20, the practitioner preferably measures the distance between the intended points of attachment of the force module 20 to the buccal tubes, brackets or other structure in the patient's oral cavity when the patient's jaws are closed. Next, the third member 26 is trimmed as needed. The collar 46 is then placed over the member 26 so that the distal end of the collar 46 is in a location to provide the desired degree of compression of the spring 42 when the patient's jaws are closed after installation of the force module 20.

In the embodiment shown in FIGS. 1–3 and 7–8, the collar 46 does not abut the second connector 48 and consequently is fixed to the third member 26 by, for example, a welding, brazing or crimping operation. Alternatively, however, the collar 46 may be of a length sufficient to abut the second connector 48 and, in that instance may merely surround the third member 26 without being fixed to the same. The latter alternative enables the practitioner to change the collar 46 if desired to use a collar of a different length after the force module 20 is removed from the oral cavity.

To complete installation, the second connector 48 is preferably secured by crimping the arms 50 to a closed orientation surrounding the lower archwire 52. subsequently, the upper connector 30 is secured to the buccal tube 54 by inserting the pin 34 through the distal opening of the buccal tube 54, and then moving the pin in a mesial direction until the spring 42 is compressed to a desired extent. Finally, the outer end section of the pin 34 is bent in an arc as described earlier in order to secure the connector 30 to the buccal tube 54.

The force module 20 may be used in an active spring mode or in a repositioning mode as chosen by the practitioner. In practice, the extent of compression of the spring 42 during installation of the force module 20 when the jaws are postured as desired determines whether the force module 20 is used in an active spring mode or in a repositioning mode. When used in an active mode, the overall effective length of the force module 20 is selected so that the first and second members 22, 24 are not fully compressed and the second member 24 is not fully inserted into the first member 22 when the patient's jaws are closed. In the active mode, the inherent bias of the spring 42 provides the desired corrective forces by urging the members 22, 24 away from each other to thereby move one dental arch relative to the other. As an example of use of the force module 20 in the active mode, approximately 1–2 mm. of compression of the spring 42 may remain available when the patient's jaws are fully closed.

In the repositioning mode, the effective length of the force module 20 is chosen so that the second member 24 is fully inserted into the first member 22 and thereby reaches a solid stop just slightly before the jaws reach their fully closed position. The lower dental arch is then moved to its corrected, desired position by the force module 20 as full jaw closure is attained. In this mode, the force module 20 functions somewhat similar to the devices described in U.S. Pat. Nos. 3,798,773, 4,462,800 and 4,551,095 mentioned above except that the increasing force of the compressed spring 42 as the force module 20 is retracted helps to urge the dental arches to their desired corrected orientation prior to reaching the hard, solid stop that occurs once the spring 42 is fully compressed.

The overall length of the force module 20 when fully compressed as well as the distance between the desired points of attachment to the patient's upper and lower dental arches determines whether the force module 20 is used in an active mode or in an repositioning mode during orthodontic treatment. The overall effective length of the force module 20 may be altered as described above by modifying the overall length of the third member 26 or by bending the third member 26 in the manner described above. In addition, the overall effective length of the device 20 may be altered by changing the configuration of the connectors 30, 48 and/or any associated components (such as the pin 34), or by changing the length of the collar 46 as mentioned above.

Other alternatives are also possible for varying the overall length of the force module 20. For example, the third member 26 may comprise a threaded cylinder that is slidably received in the second member 24 and a solid, externally threaded rod that is threaded into the cylinder. Other types of threaded assemblies that may instead be used include threaded rods and nut assemblies. Alternatively, the third member 26 may comprise a rod that is slidably received in a mating cylinder which is then crimped by the practitioner as desired to provide a certain selected length. As other alternatives, the length of one or both of the members 22, 24 can be altered.

As correction of the malocclusion is accomplished during the course of treatment, the practitioner may elect to increase the effective length of the force module 20 to ensure that the force exerted on the patient's jaws remains effective. The effective length may be increased by removing the force module 20 and then changing the third member 26 or by the means described in the preceding paragraphs. Alternatively, the practitioner can simply crimp on a split tube to the third member 26 in the space between the collar 46 and the fitting 44.

As the patient's jaws are opened, the spring 42 urges the members 22, 24 in opposite directions until such time as the enlarged inner end portion 40 of the second member 24 comes into contact with the inner, narrowed end portion 28 of the first member 22. Once such contact occurs, further widening of the patient's jaws causes the third member 26 to move away from the second member 24 as shown in FIG. 8. The third member 26 is freely slidable within the second member 24 and is not urged outwardly by the spring 42 independently of movement of the member 24.

Preferably, the overall lengths of the members 22, 24, 26 are selected so that the third member 26 does not fully withdraw and separate from the second member 24 when the patient's jaws are fully opened. The use of three members 22, 24, 26 is an advantage in that the third member 26 need not be secured to the second member 24, and yet does not separate from the second member 24 once installed in the oral cavity. Such construction is in contrast to some of the conventional telescoping force modules mentioned above where, under some circumstances, the plunger can be detached from the cylinder when the patient's jaws are fully opened.

The provision of three members 22, 24, 26 also facilitates sliding, telescopic movement during use of the force module 20, since a significant section of each member 22, 24, 26 is always in contact with the adjacent member or members. Such overlapping contact reduces "cocking" of one member 22, 24, 26 relative to adjacent members and as a result excessive frictional binding during sliding movement is avoided.

The connectors 30, 48, in combination with the generally "L"-shaped pin 34, allow pivotal movement of the force module 20 about the longitudinal axes of the archwires 52, 58 so that lateral excursions of the patient's jaws are not unduly hindered. In particular, the outer end section 38 of the pin 34 is free to rotate about its central axis in the passage of the upper buccal tube 54, and the clearance space between the cinched arms 50 and the adjacent portion of the lower archwire 58 allows the force module 20 to freely move as needed during lateral or side-to-side movement of the mandibular jaw.

Optionally, the force module 20 may include a second coil spring that is installed between the fitting 44 and the collar 46 or the second connector 48. An example of such construction is shown in FIG. 1a wherein a force module 20' is identical to the force module 20 described above, except that the force module 20' lacks a collar and includes a second coil spring 43' that extends between a fitting 44' and a second connector 48'. The overall length of the spring 43' when fully compressed (as shown) serves as a stop and hence a collar is not needed. In all other aspects, the force module 20' is equivalent to the force module 20.

In the force module 20', the spring constant of the second spring 43' is preferably selected to provide a spring force different than the force provided by a first coil spring 42'. For example, the second spring 43' could be relatively stiff, such that the force module 20' exerts an increased level of force once the patient's jaws are moved past a certain relative position and the first spring 42' is fully compressed as the patient's jaws are closed.

The intra-oral force module 20 according to the invention is normally used in pairs. The force module 20 illustrated in FIGS. 7 and 8 is shown as mounted on the right side of the patient's jaws. A somewhat similar force module that is a mirror image to the force module 20 is mounted on the left side of the patient's jaws and is connected to adjacent appliances similar to the upper buccal tube 54 and the lower archwire 58.

In FIGS. 7 and 8, the second connector 48 is slidably coupled to the archwire 58 in the space between adjacent brackets 56. Optionally, a crimpable stop or other force module can be fixed to the archwire 58 or to the mesial bracket 56 to serve as an abutment for the connector 48 and limit movement of the connector 48 in a mesial direction during jaw closure. As another option, the connector 48 may be secured to the distal side of the mesial bracket 56 using, for example, a section of ligature wire or the like.

Installation of the force module 20 in the manner shown in FIGS. 7 and 8 enables the spring 42 to urge the mandibular dental arch in a forwardly direction when the jaws are closed, as is desirable when correcting a Class II malocclusion. As an alternative, however, the force module 20 may be used for correction of a Class III malocclusion by inverting the force module 20 from its orientation shown in FIGS. 7 and 8. In the inverted orientation, the pin 34 serves to couple the connector 30 to the lower buccal tube 60 and the second connector 48 is crimped to a section of the upper archwire 52 in a space between an adjacent pair of brackets 56.

Figure 9:
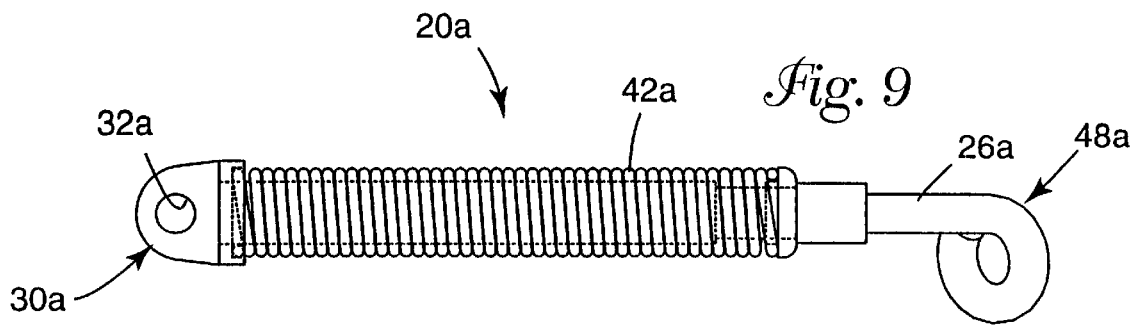
FIG. 9 is a side elevational view of a telescoping intra-oral force module device according to another embodiment of the invention.

FIG. 9 is an illustration of an alternate embodiment of the invention, wherein a force module 20a includes a first elongated, tubular member, a second elongated, tubular member and a third elongated member 26a that is preferably solid. A spring 42a extends around the first and second members for urging the first and second members in directions away from each other.

The first, second and third members are essentially identical to the first, second and third members 22, 24, 26 described above, and other aspects of the force module 20a are essentially identical to the force module 20 except for the connectors 30a, 48a. As shown in FIG. 9, the connector 30a includes a tab portion that extends outwardly from the first member in a direction along the longitudinal axis of the latter. The connector 30a includes a hole 32a for receiving a pin (not shown) that preferably is identical to the pin 34 described above.

The connector 48a is different than the connector 48, in that the connector 48a is integrally connected to the third member 26a. Preferably, the connector 48a is formed by annealing an elongated wire body that also includes the third member 26a and then bending an outer end section of the body in a loop. The loop may be left in a slightly open orientation until such time as the force module 20a is installed in the patient's oral cavity. The loop is then crimped to a closed position as shown in FIG. 9 once the archwire has been received in the c(enter of the loop.

Figure 9A:
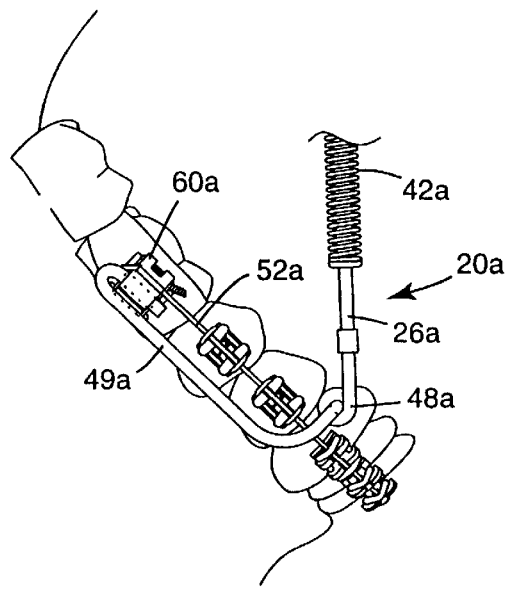
FIG. 9a is a fragmentary, reduced side view in partially schematic form of the force module illustrated in FIG. 9 when installed in the oral cavity of a patient and additionally showing an optional cantilever device for connecting the force module to a buccal tube mounted on one of the patient's molar teeth.

FIG. 9a is a fragmentary illustration of the force module 20a when installed in the oral cavity of a patient. However, in FIG. 9a the connector 48a is coupled to a cantilever device 49a that serves to attach the third member 26a to a lower buccal tube 60a. As shown, the distal portion of the cantilever device 49a has a generally "J"-shaped configuration with a cylindrical free end that is slidably received in a cylindrical passage of the buccal tube 60a. The major extent of the cantilever device 49a extends below and in parallel relation to an archwire 52a. A mesial portion of the cantilever device 49a extends upwardly and terminates in a lingually-extending section that passes through the connector 48a.

The cantilever device 49a may also be used with force modules according to other embodiments of the invention, such as the force module 20 described above. Moreover, the cantilever device 49a may have other configurations as well, such as the various configurations described in U.S. Pat. No. 5,718,576, which is incorporated by reference.

A force module 20b according to another embodiment of invention is illustrated in FIGS. 10–13. The force module 20b includes an elongated first member 22b, an elongated second member 24b and an elongated third member 26b (FIG. 12). In FIG. 11, the longitudinal axis of the first member 22b is designated by the numeral 64b, while the longitudinal axes of the second and third members 24b, 26b are coaxial and are designated by the numeral 66b.

The first member 22b preferably includes a solid section 68b and a tubular section 70b that are securely fixed to each other. For example, the solid section 68b may be made from a section of stiff, cylindrical wire stock, and the tubular section 70b may be soldered, brazed, or welded to the solid section 68b. Alternatively, the solid section 68b and the tubular section 70b may be integrally made in a metal casting process or by a metal injection molding process.

The second member 24b includes a first tubular section 72b and a second tubular section 74b that is substantially shorter in length than the first tubular section 72b. The tubular sections 72b, 74b are preferably cut from tubular stock and then securely fixed to each other by a soldering, brazing or welding process. Alternatively, the tubular sections 72b, 74b can be integrally joined together and made in a metal casting process or by a metal injection molding process.

The third member 26b is preferably made from a section of stiff solid wire stock. Preferably, the outer wall surfaces of the third member 26b, the solid section 68b and the tubular section 72b have a cylindrical configuration. Preferably, the inner wall surfaces of the tubular sections 70b, 74b, 72b are also cylindrical and have a diameter that is just slightly greater than the outer diameter of the tubular section 72b, the solid section 68b and the third member 26b respectively.

A coiled compression spring 42b surrounds the second member 24b and has one end that bears against the tubular section 70b. The opposite end of the spring 42b bears against an annular fitting 44b that is secured to an end portion of the second member 24b at a location remote from the first member 22b. The fitting 44b may be made by flaring or swaging the outer end portion of the second member 24b or alternatively may be an initially separate element that is crimped, brazed, welded or otherwise secured to the outer end portion of the second member 24b.

The spring 42b serves to urge the members 22b, 24b in opposite directions away from each other. In FIG. 10, the force module 20b is shown as fully condensed, with the spring 42b fully compressed between the fitting 44b and the tubular section 70b. In FIG. 11, the members 22b, 24b have moved away from each other under the influence of the spring 42b to their outer limit of travel, which is determined by the location where the tubular section 70b contacts the tubular section 74b. During relative movement of the members 22b, 24b, the solid section 68b slides within the tubular section 74b along the first axis 64b while the tubular section 72b simultaneously slides within the tubular section 70b along the second axis 66b.

Additionally, the third member 26b is free to slide in the tubular section 72b. The third member 26b is shown in FIG. 11 in a position representing the inwardly limit of travel in a direction toward the first member 22b, and is illustrated for exemplary purposes in FIG. 12 in an extended position. Preferably, the third member 26b can be completely withdrawn and separated from the second member 24b for any necessary adjustments such as bending or trimming before the force module 20b is installed in the patient. Once installed, however, the lengths of the members 22b, 24b, 26b are sufficient to prevent complete withdrawl of the third member 26b from the second member 24b even when the patient's jaws are fully opened.

The force module 20b also has a first connector 30b and a second connector 48b. The first connector 30b is preferably integral with the first member 22b and is constructed by bending a section of stiff cylindrical wire into a partially closed loop and also forming a 90° bend inwardly of the loop. The second connector 48b is preferably identical to the first connector 30b. Optionally, the practitioner may form the second connector 48b in the operatory after first determining the optimal overall effective length of the force module 20b and then trimming the wire section as needed.

Once the force module 20b is in place in the patient's oral cavity, the partially closed loops are received around sections of archwire, such as a section of archwire next to the mesial side of a buccal tube mounted on the patient's upper right first molar tooth and a section of archwire next to the mesial side of a bracket mounted on the patient's first lower right bicuspid tooth. Other installation positions are also possible. The loops are then crimped to a closed position to capture the connectors 30b, 48b to the upper and lower archwires respectively. Alternatively, a pin such as the pin 34 described above may be used in conjunction with the looped connectors 30b, 48b for coupling the force module 20b to a buccal tube, bracket or other appliance that is secured to the patient's tooth structure. Moreover, other connectors such as the connectors 30, 48 may instead be employed.

In other aspects, the force module 20b functions in a manner similar to the force modules 20, 20a. The provision of dual offset tubular sections 70b, 74b facilitates free sliding relative movement of the members 22b, 24b under the bias of the spring 42b when the patient's jaws are opened.

In all of the aforementioned variations of the invention, the external spring 42, 42a, 42b is an advantage over internal springs, in that the external spring can be somewhat larger in diameter and length and consequently operate at significantly lower stress levels in comparison to an internal spring offering an equivalent spring force. Such lower stress levels greatly reduce the possibility of spring breakage due to premature fatigue failure. Moreover, the external nature of the spring 42, 42a, 42b as well as other components of the force module 20, 20a, 20b promotes good hygiene by reducing areas where food and other material may be trapped.

Preferably, all of the elements of the force module 20, 20a, 20b are made of corrosion resistant materials that provide satisfactory service in the oral environment. Suitable materials include, for example, stainless steels such as AISI 300 series types (including 302 or 304), although other materials may also be employed.

In addition, it may be apparent to those skilled in the art that a number of modification and additions may be made to the force modules described above without departing from the spirit of the invention. Accordingly, this invention should not be deemed limited to the presently preferred embodiments that are set out in detail above, but instead only by a fair scope of the claims that follow along with their equivalents.

I claim:

1. An intra-oral force module for moving the relative positions of the mandibular and maxillary dental arches comprising:

a first tubular member;

a second tubular member having a portion slidably received in the first member and being movable relative to the first member;

a third member having a portion slidably received in the second member; and a helical spring extending around the second member for urging the second member and the first member in directions away from each other.

2. An intra-oral force module according to claim 1 wherein the third member is solid.

3. An intra-oral force module according to claim 1 wherein the third member has an effective overall length that is variable.

4. An intra-oral force module according to claim 3 wherein the third member includes a threaded rod.

5. An intra-oral force module according to claim 1 and including a connector that is crimped to the first member or the third member.

6. An intra-oral force module according to claim 1 wherein the third member is curved in direction along its longitudinal axis.

7. An intra-oral force module according to claim 1 wherein the second member has an enlarged end portion that functions as a stop to limit outwardly movement of the second member relative to the first member.

8. An intra-oral force module according to claim 1 and including a connector coupled to an end portion of the first member, and wherein the spring bears against the connector.

9. An intra-oral force module according to claim 1 wherein the third member is freely slidable relative to the second member.

10. An intra-oral force module according to claim 1 wherein the third member is detachable from the second member before installation of the force module in the oral cavity.

11. An intra-oral force module according to claim 1 wherein the third member includes a collar that limits movement of the third member in directions toward the first member.

12. An intra-oral force module according to claim 1 wherein the first member, the second member and the third member all have colinear central axes.

13. An intra-oral force module according to claim 1 wherein the longitudinal axis of the first member is offset from the longitudinal axis of the third member.

14. An intra-oral force module according to claim 1 wherein the spring also extends around the first member.

15. An intra-oral force module according to claim 1 and including a second helical spring that extends around the third member.

16. An intra-oral force module according to claim 15 wherein the second spring provides a force different than the force provided by the spring extending around the second member.

17. An intra-oral force module for moving the position of one dental arch relative to the other comprising:

an elongated first member having a tubular section and an outer end portion for connection to one of the patient's dental arches;

a second elongated member having a tubular section and received at least partially in the tubular section of the first member, the second member being longitudinally slidable in the tubular section of the first member;

a third elongated member received at least partially in the tubular section of the second member and being longitudinally slidable in the tubular section of the second member, the third member having an outer end portion for connection to the remaining dental arch of the patient; and a spring extending externally around the second member, wherein the spring has a first end portion connected to the first member and a second end portion connected to the second member for urging the first member and the second member in directions away from each other.

18. An intra-oral force module according to claim 17 wherein the third member is solid.

19. An intra-oral force module according to claim 17 wherein the third member has an effective overall length that is variable.

20. An intra-oral force module according to claim 17 and including a connector that is crimped to the first member or the third member.

21. An intra-oral force module according to claim 17 wherein the second member has an enlarged end portion that functions as a stop to limit outwardly movement of the second member relative to the first member.

22. An intra-oral force module according to claim 17 and including a connector coupled to an end portion of the first member, and wherein the spring bears against the connector.

23. An intra-oral force module according to claim 17 wherein the third member is freely slidable relative to the second member.

24. An intra-oral force module according to claim 17 wherein the third member includes a collar that limits movement of the third member in directions toward the first member.

25. An intra-oral force module according to claim 17 wherein the first member, the second member and the third member all have colinear central axes.

26. An intra-oral force module according to claim 17 wherein the longitudinal axis of the first member is offset from the longitudinal axis of the third member.

27. An intra-oral force module according to claim 17 and including a second helical spring that extends around the third member.

28. An intra-oral force module according to claim 27 wherein the second spring provides a force different than the force provided by the spring extending around the second member.

* * * * *